United States Patent [19]
McRae

[11] Patent Number: 5,193,468
[45] Date of Patent: Mar. 16, 1993

[54] MEDICAL WASTE INCINERATOR

[75] Inventor: Harrell J. McRae, Huffman, Tex.

[73] Assignee: Texas Refractory Service, Inc., Huffman, Tex.

[21] Appl. No.: 828,343

[22] Filed: Jan. 30, 1992

[51] Int. Cl.⁵ .............................................. F23G 7/06
[52] U.S. Cl. ...................................... 110/235; 110/212
[58] Field of Search ............... 110/235, 211, 212, 213, 110/214, 256, 229, 248

[56] References Cited
U.S. PATENT DOCUMENTS 3,808,619 5/1974 Vanderveer .................... 110/213
4,280,417 7/1981 Alexandersson ............. 110/248 X
4,966,086 10/1990 Houston ....................... 110/248 X Primary Examiner—Edward G. Favors
Attorney, Agent, or Firm—Head & Johnson

[57] ABSTRACT

A medical waste incinerator with primary and secondary incinerator chambers. The primary chamber has an "hour-glass" shape and air conduits that are directed downward to prevent clogging. There are no interior metal structures within the burning chambers. The primary incineration chamber uses sub-stoichiometric amounts of air.

10 Claims, 7 Drawing Sheets

MEDICAL WASTE INCINERATOR

BACKGROUND OF THE INVENTION

1. Field of the invention

This invention relates to the field of waste incineration. More specifically it relates to medical waste incinerators that have 100% burn efficiency, no interior metal parts, and two separate burners.

2. Description of the related art

Disposal of medical wastes is an increasing problem in our society. Various way of dealing with this have been proposed: encapsulating in resin (U.S. Pat. No. 4,919,569), heating and encapsulating in heat activated plastic (U.S. Pat. No. 4,992,217), grinding waste and adding sterilizing fluid (U.S. Pat. Nos. 4,979,683; 5,035,367), crushing (U.S. Pat. No. 5,035,367) and irradiation (U.S. Pat. No. 5,035,858). However, incineration remains the major method of destroying medical and other waste.

Incineration of materials has several problems. Build up of slag on the furnace walls can clog outlets, and decrease efficiency. Various methods have been tried to solve these problems: adding metals with high melting points to reduce adherence of slag (U.S. Pat. No. 4,953,481), forcing air or mechanical means through ports to unclog them (U.S. Pat. Nos. 3,867,909; 3,900,011). Likewise, various configurations of incinerators have been used. Many use grates (U.S. Pat. Nos. 4,006,693; 4,321,879; 4,430,948)—but grates may burn up, break, or become clogged. Caps over outlets and ports hinder cleanout and may break. Ports in the floor or sidewalls of many incinerators are subject to clogging with ash, melted plastic or slag which interferes with air flow and burning and requires shutdown of the unit to clean out the ports. Air tubes may be inserted into the chamber, but are usually rapidly destroyed by the corrosive action of acids in the wastes and by the intense heat.

Medical and biohazardous waste is often a special problem since it is usually non-homogeneous waste; i.e. it may include liquids and/or solids such as paper, plastic, fabric, biological tissues, metal, glass, and the like. Many incinerators do not fully burn such mixed composition waste.

SUMMARY OF THE INVENTION

It is an object of this invention to provide an incinerator which has no interior metal parts.

It is another object of this invention to provide an incinerator which has no grate.

It is a further object of this invention to provide an incinerator in which air injection tubes do not become clogged.

It is yet a further object of this invention to provide air or gas injection tubes that point generally downwardly into the lower burning chamber.

It is another object of this invention to provide an incinerator which results in a total or 100% burn.

It is an object of this invention to provide an incinerator that is suitable for medical, biomedical, and hazardous waste incineration.

It is an object of this invention to provide an incinerator with primary and secondary incinerating chambers.

It is an object of this invention to provide an incinerator with a secondary incinerating chamber which has means therein to lengthen the burning path.

It is another object of this invention to provide an incinerator that has automatic controls and feedback circuits.

In the preferred embodiment, bagged waste, such as "Red Bag" medical waste is placed in a feed chute. A door to the primary incinerator is opened and the waste pushed into the chamber then the door is closed. Various parameters are set on the control panel, such as temperature, time of burn, fuel and air pressure, and the like. The chamber has an "hourglass-like" configuration with an upper portion and a lower portion. The upper portion has a downwardly sloping bottom on which the waste bags rest and slide toward a central constricted passage which connects to the lower portion of the primary incinerator. The lower, primary incinerator, portion has a burner and air injection ports. The air injection ports and conduits are located within the insulated walls of the chamber and are directed downwardly toward the floor of the lower portion. This precludes clogging of the air ports. Also, the configuration of the constricted lower portion in which primary burning occurs, confines air and fuel to create total burning and mixing of components. Sub-stoichiometric amounts of air are used in the primary incinerator, with stoichiometric or excess amounts of air being used in a secondary incinerator.

The burned waste, gases, and residues rise through the upper portion of the primary incinerator and pass, by means of a stepped pipe, into the secondary incinerator located on top of the primary incinerator. This secondary incinerator also has a burner and air intakes. The chamber of this secondary incinerator has a baffle therein to direct flow to provide a longer burn path. The burn products are then vented to the outside via an exhaust means.

These objects are meant to be illustrative and not limiting. The manner of operation, novel features and further objectives and advantages of this invention may be better understood by reference to the accompanying drawings, description and claims.

DESCRIPTION OF THE PREFERRED EMBODIMENT

Figure 1:
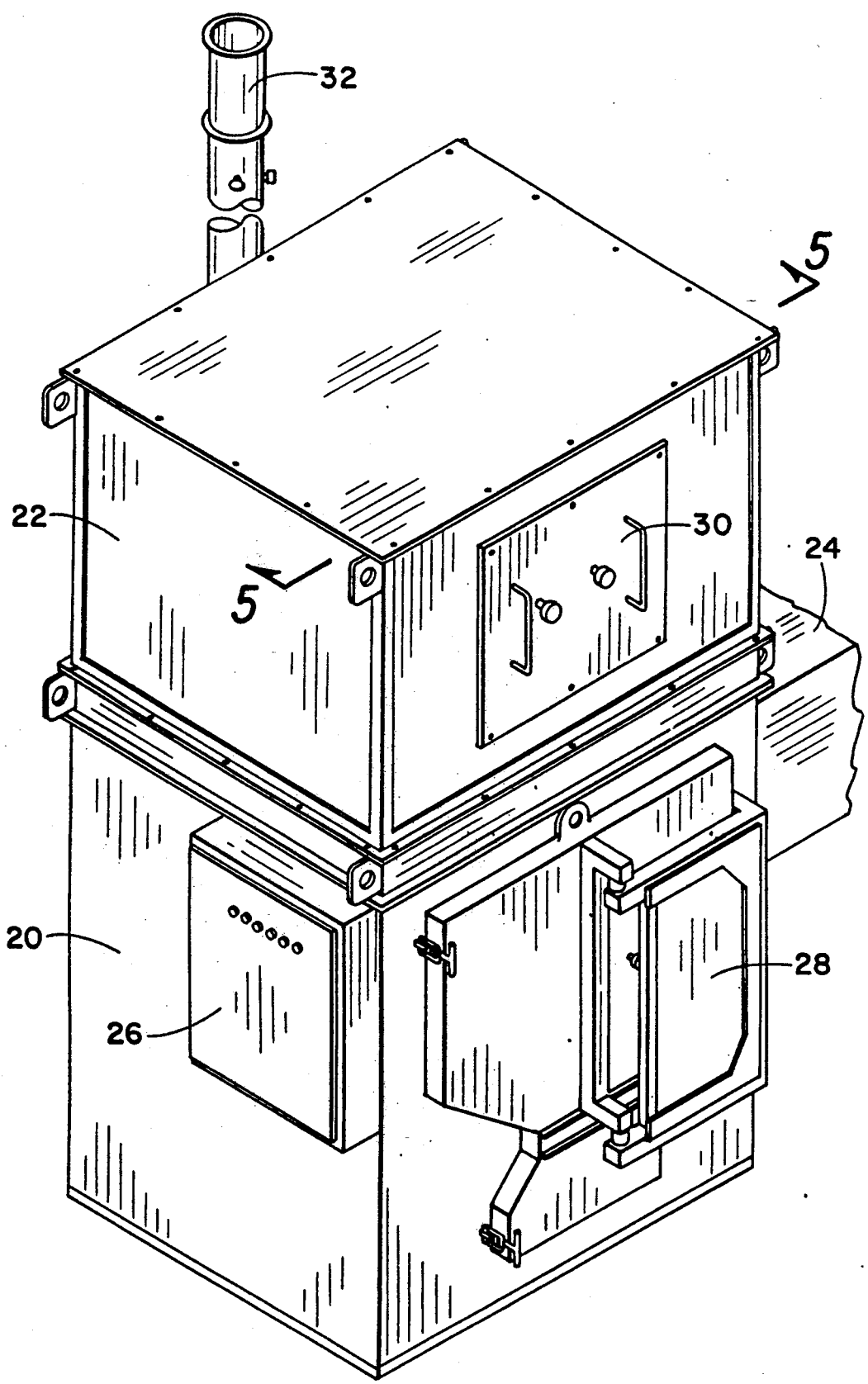
FIG. 1 is a perspective view.

FIG. 1 is an exterior perspective view of the incinerator. This comprises a primary incinerator, generally indicated at 20 and a secondary incinerator located upon the primary incinerator, generally indicated at 22. The primary incinerator 20 has a feed or load chute 24 through which waste is introduced into the primary incinerator 20; a control panel 26; and a primary incinerator door 28 which may be opened to clean out the primary incinerator chamber and/or to provide access to the interior thereof. The secondary incinerator 22 has a secondary incinerator door 30 which permits access to the secondary incinerator chamber; and a flue stack 32 that functions as a vent or exhaust means.

Figure 2:
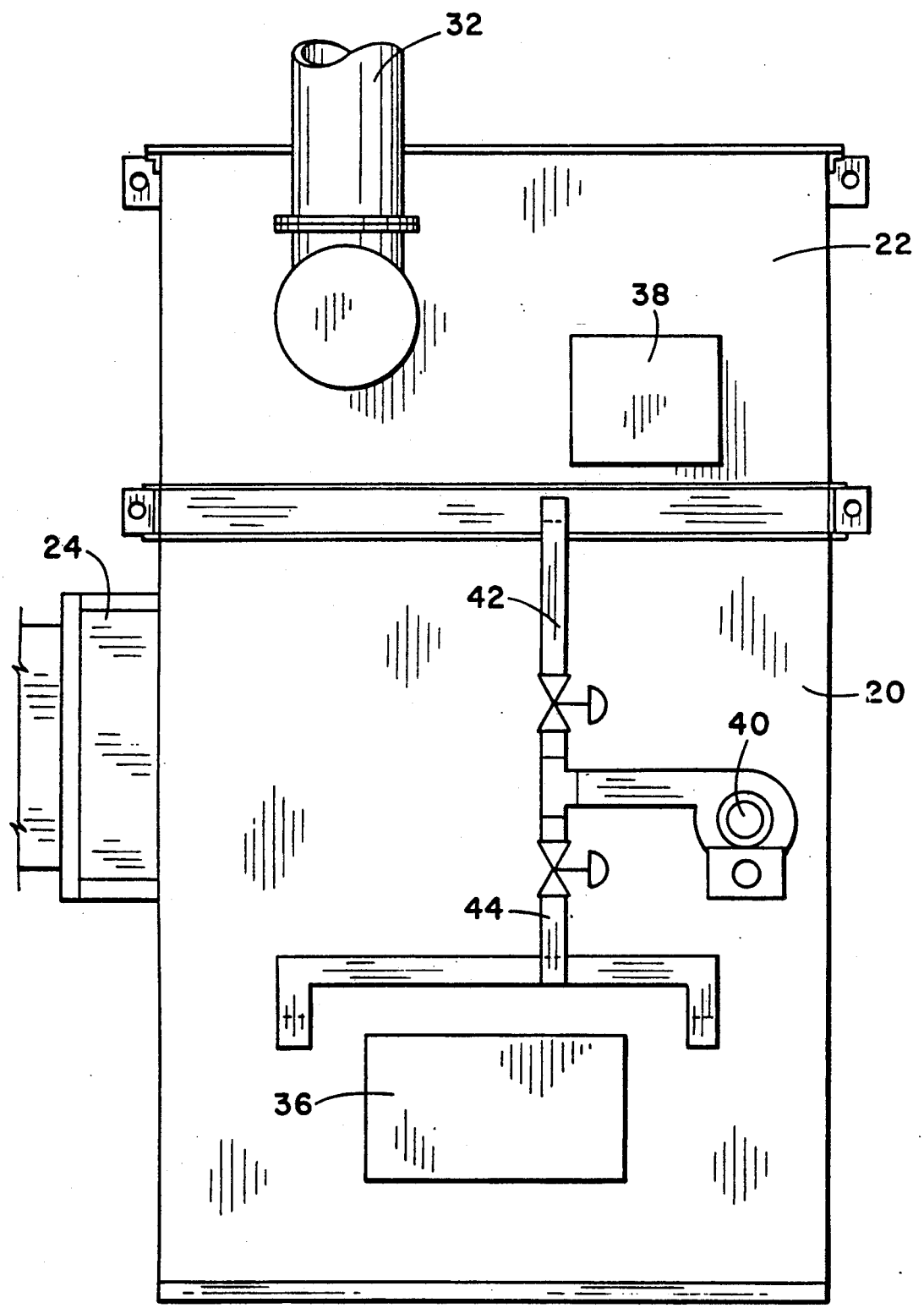
FIG. 2 is a rear elevational view.

FIG. 2 is an exterior rear elevational view of the incinerator. The primary incinerator 20 and secondary incinerator 22 are shown. The feed or load chute 24 and the flue 32 are also seen. In addition, the lower burner 36 which supplies combustion to the primary incinerator 20, and the upper burner 38 which supplies combustion to the secondary incinerator 22, are illustrated. An air blower 40 is connected to a pipe to the upper air ducts 42 and a pipe to the lower air ducts 44.

Figure 3:
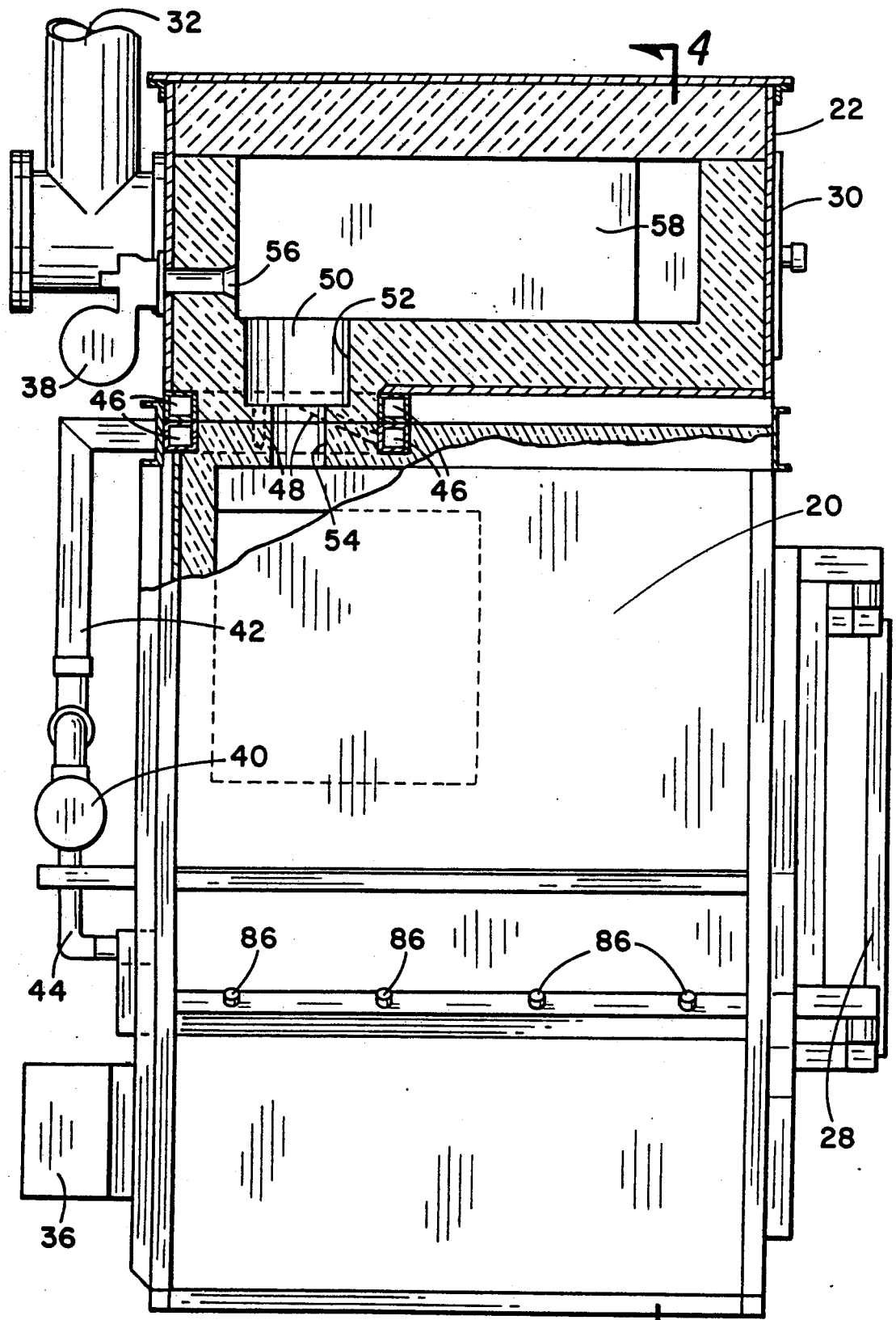
FIG. 3 is left side elevational view with partial cut away.

FIG. 3 is a left side elevational view with partial cut away of the secondary incinerator. This illustrates the upper air pipe 42 going to a series of ducts 46 from which air conduits (shown in dotted outline at 48 feed into a stepped pipe or passageway 50, which connects the primary incinerator 20 and the secondary incinerator 22. Several details of the stepped pipe 50 are noted—this comprises a large diameter upper portion 52 and a smaller diameter lower portion 54; also, the air conduits 48 feed into the stepped pipe 50 at an upwardly facing angle (this configuration is shown in greater detail in FIGS. 5, 6 and 7). This configuration causes turbulence and thus enhances combustion.

Still in FIG. 3, the upper gas burner 38 is noted with its port 56 entering the secondary incinerator 22. The flow of burn products from the stepped pipe 50, with admixed air from air conduits 48, rises to pass the burner port 56 creating further turbulence and enhanced combustion. A baffle 58 is present in the secondary incinerator which creates a longer dwell time, and a longer burn path further enhancing complete combustion. Thus, the burn products from the primary incinerator 20 pass through the stepped pipe 50, into the secondary incinerator 22, around the baffle 58, and are then exhausted through the flue 32.

Figure 4:
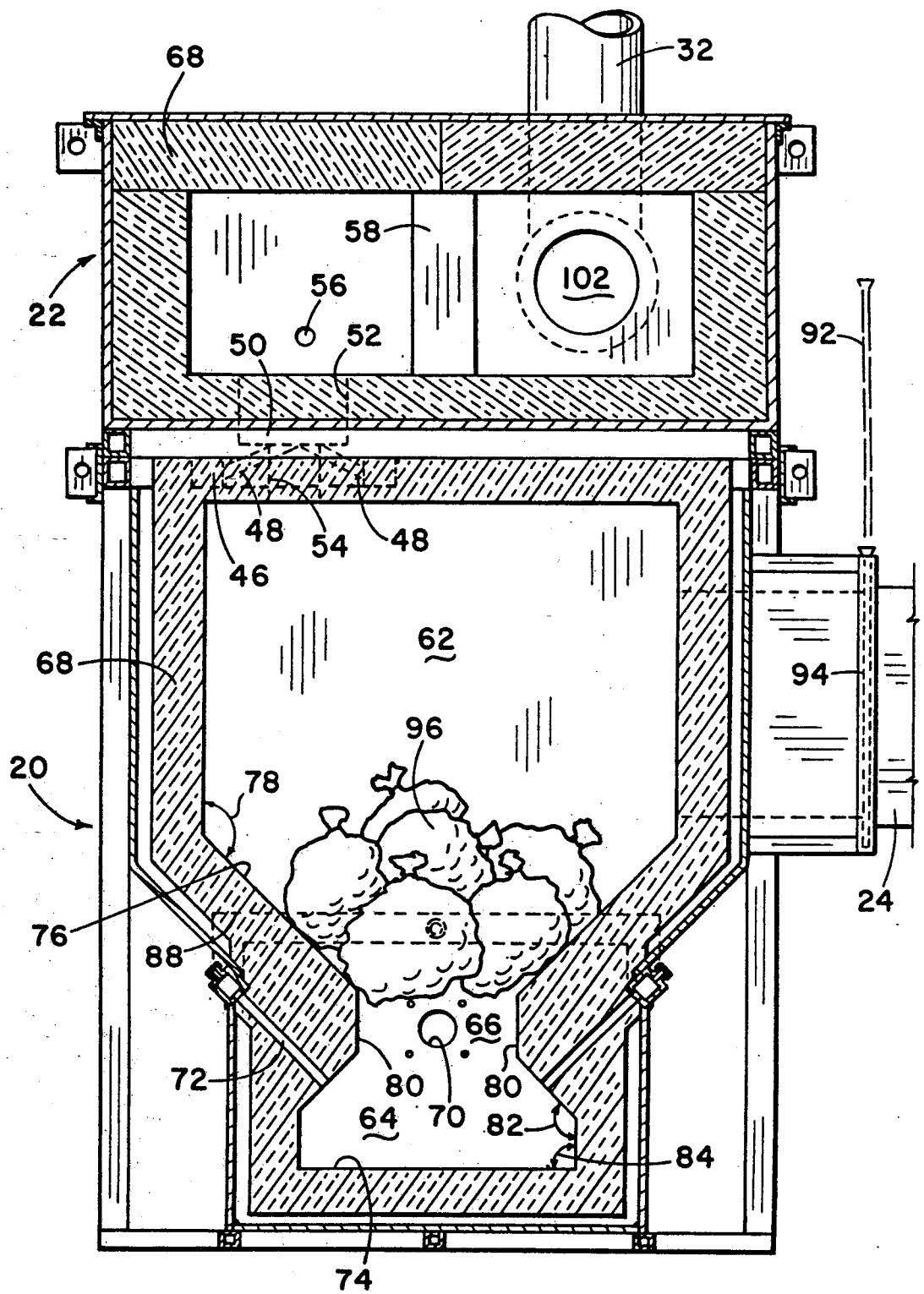
FIG. 4 is a sectional view along line 4—4 in FIG. 3.

FIG. 4 is a sectional view along line 4—4 in FIG. 3. In the primary incinerator 20 a bifurcated chamber is shown with a dilated upper portion 62 and a smaller dilated lower portion 64. These two dilated portions, 62 and 64 are connected by a constricted area 66 forming a neck-like or choke-like passage between the two dilated portions 62 and 64. In general outline this is suggestive of an hourglass shape. The entire inner surface is lined by insulation 68. The insulation comprises a two inch layer of block insulation over all surfaces, which is then covered with an additional 4 to 7 inches of refractory lining of high alumina castable insulation with a rating of 3000 degrees Fahrenheit. The insulation is anchored with refractory or alloy type anchors on 9 to 12 inch centers.

Still at FIG. 4, the lower portion 64 of the primary incineration chamber shows the lower burner port 70 and air conduits 72. The air conduits 72 are placed in the insulated wall 64 of the lower portion 64 and are pointed downwardly so that air flow is generally directed toward the floor 74 of the lower portion 64. The constricted area 66 between the two portions 62 and 64 has a downwardly sloping top surface 76 which forms a sloping shelf on which waste is deposited and slides toward the constricted opening 66. The angle at 78 is obtuse, and in the preferred embodiment is approximately 135 degrees. This angle 78 may be greater or smaller depending on the type of waste to be burned. The sloping top surface 76 slopes downward to end at the constricted opening 66 between the two portions 62 and 64. The side walls 80 of the constricted passage 66 are parallel to each other, and generally perpendicular to the floor 74 of the lower portion 64. Still in the lower portion 64, angle 82 is obtuse and angle 84 is a right angle.

FIG. 4 also shows details of the air delivery system to the chamber in the lower portion 64. The air conduits 72 have a threaded cap 86 which may be removed for cleaning or repair. The supply of air comes from a manifold 88 indicated by dotted lines which is connected to the lower air pipe 44 (seen in FIG. 3). Thus, in operation, air (or other gas supporting combustion) is fed under pressure into the manifold 88 and through the air conduits 72 into the lower portion 64 of the chamber. There the air mixes with the fuel from the burner port 70 and combustion occurs. In the preferred embodiment, the air is supplied in sub-stoichiometric amounts, so that incomplete combustion occurs, thus providing unused fuel for burning in the upper portions of the chambers. The arrangement of the downwardly pointing conduits 72 in the downwardly facing undersurface 90 of the constricted area, precludes clogging of the conduits, and also causes turbulence and mixing in the lower chamber 64 promoting burning of waste and sludge.

FIG. 4 further illustrates the upper portion 62 of the primary incinerator 20. The feed chute 24 is attached, and a guillotine-type door is present. The door is shown in the up position 92 and in the down position 94, both with dotted lines. There is a feed back mechanism (well known in the art and not shown) for shutting off fuel and air to the lower chamber 64 if the door 92 is opened while burning. Waste is pushed along the chute 24, through the open door 92 into the upper portion of the chamber 62 (the opening through the insulation 68 into the chamber 62 is shown by dotted lines 100). The Waste may be manually pushed through the chute, or mechanical, hydraulic, pneumatic or other suitable means may be used. Several bags of waste 96 are illustrated resting on the sloping shelf 76. When initially loaded, the shelf 76 and neck area 66 hold the waste above the lower portion 64 of the chamber so that it (the lower portion 64) is empty and combustion may be easily started therein. Once burning has commenced the waste 96 breaks down and portions fall into the lower part of the chamber 64 and are substantially burned. The products of combustion, substantially free of ash, from the slow burning in the lower chamber pass upwardly through the upper portion 62 of the primary incinerator 20 through the small 54 and large 52 lumina (shown in dotted outline) of the stepped pipe 50 into the secondary incinerator 22. Additional air (stoichiometric amounts or more) is fed into the upwardly moving stream by the upper air conduits 48 and thence past the upper burner port 56 and along the burn path around the baffle 58 and then through the flue opening 102 and out the flue 32.

Figure 5:
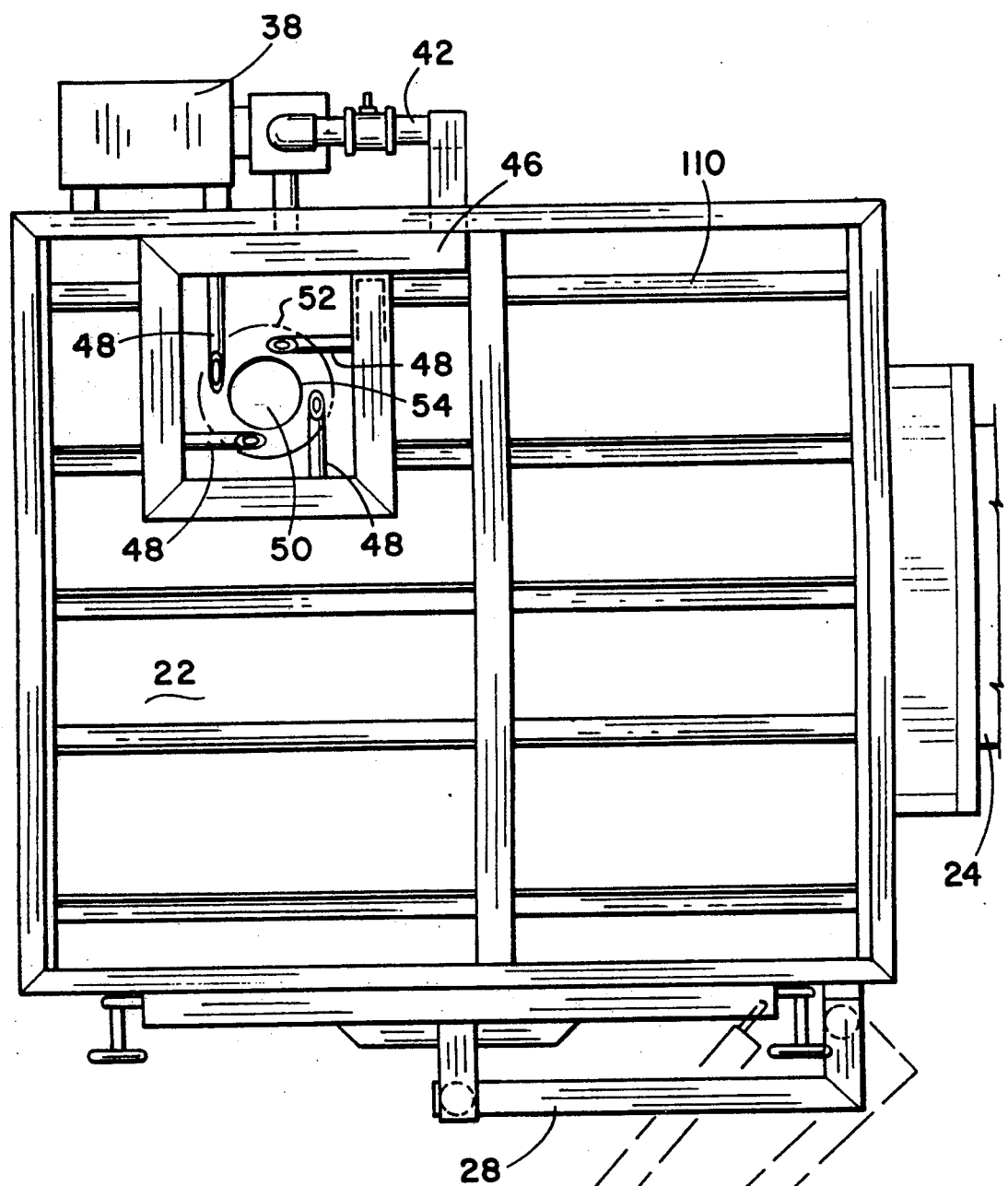
FIG. 5 is a downward sectional view.

FIG. 5 is a downward sectional view and illustrates the floor of the secondary incinerator 22 with the insulation removed, and showing supporting bars 110. Some details of the stepped pipe 50 are shown, with the large pipe 52, smaller pipe 54 and air conduits 48. The upper air supply pipe 42 is shown feeding into the air ducts 46. The primary incinerator door 28 is also shown in shut and open position 112 (in dotted outline). When the door 112 is open, it allows access to both the upper 68 and lower 64 portions of the primary incineration chamber 20 for cleaning, repairs, and the like.

Figure 6:
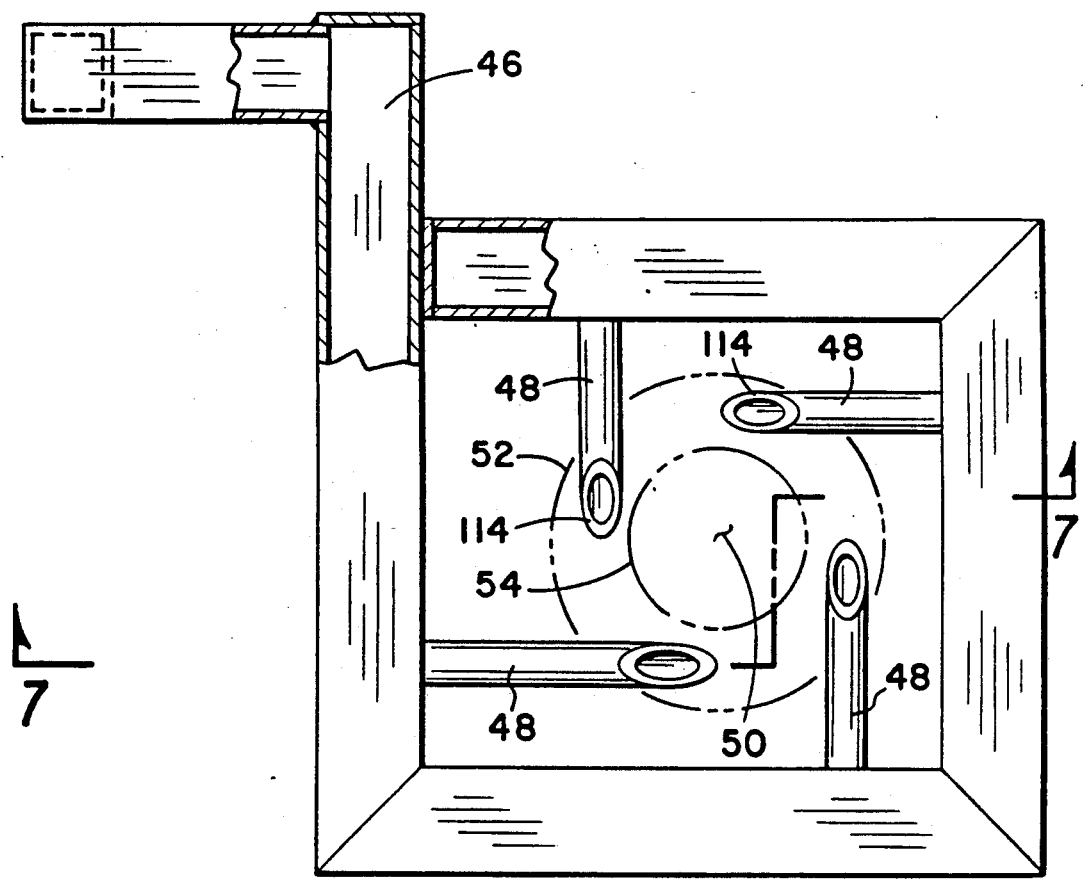
FIG. 6 is a detailed view of the stepped pipe and air vents into the secondary incinerator.

FIG. 6 illustrates the air supply and stepped pipe 50 in grater detail. The air conduits 48 are shown with upwardly facing, beveled nozzles 114 feeding into the stepped pipe 54. This creates an upward draft of air, further enhancing flow, turbulence and combustion.

Figure 7:
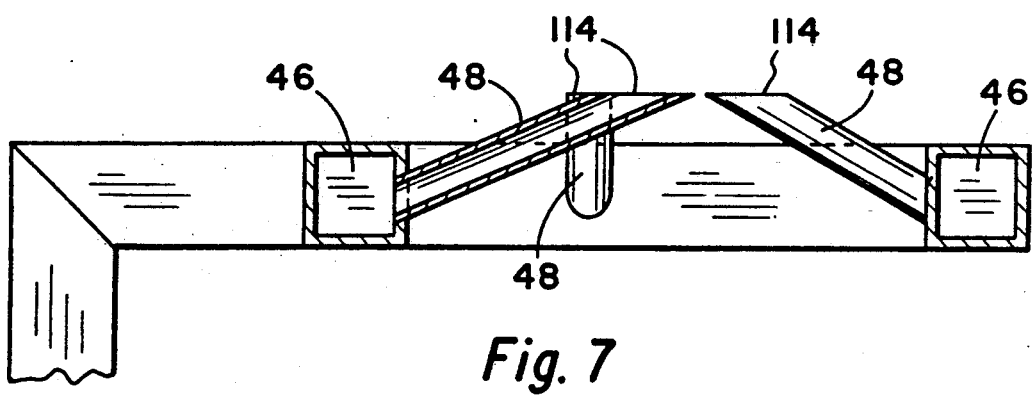
FIG. 7 is a sectional view along line 7—7 in FIG. 6.
Figure 8:
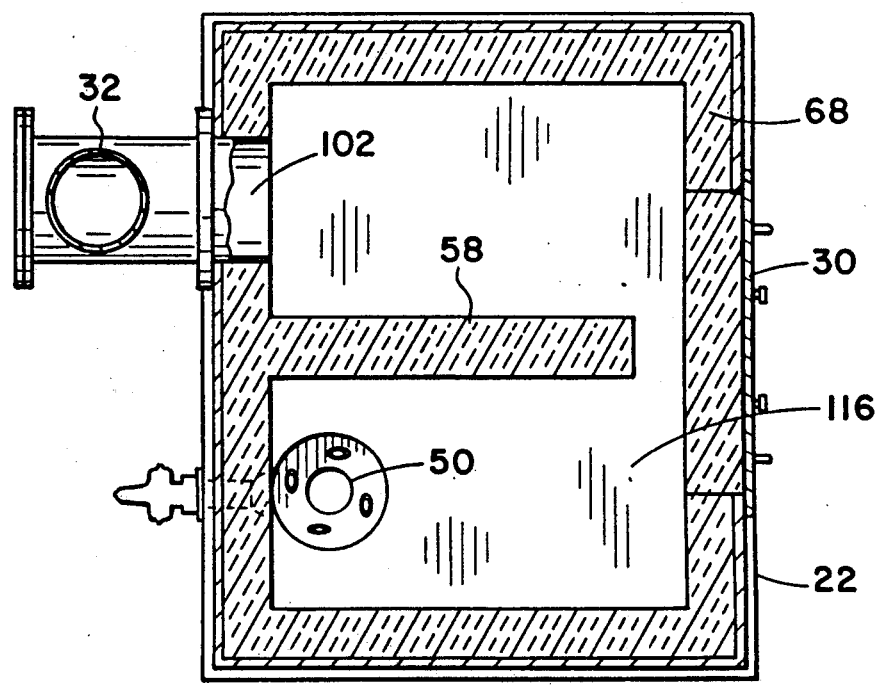
FIG. 8 is a downward sectional view of the secondary incinerator.

FIG. 7 illustrates the above configuration along line 7—7 in FIG. 6.

Figure s illustrates a top sectional view of the secondary incinerator 22. The chamber 116 is partially divided by a baffle 58 so that burn products and air coming from the stepped pipe 50 pass around the baffle 58 and out the flue 32.

Figure 9:
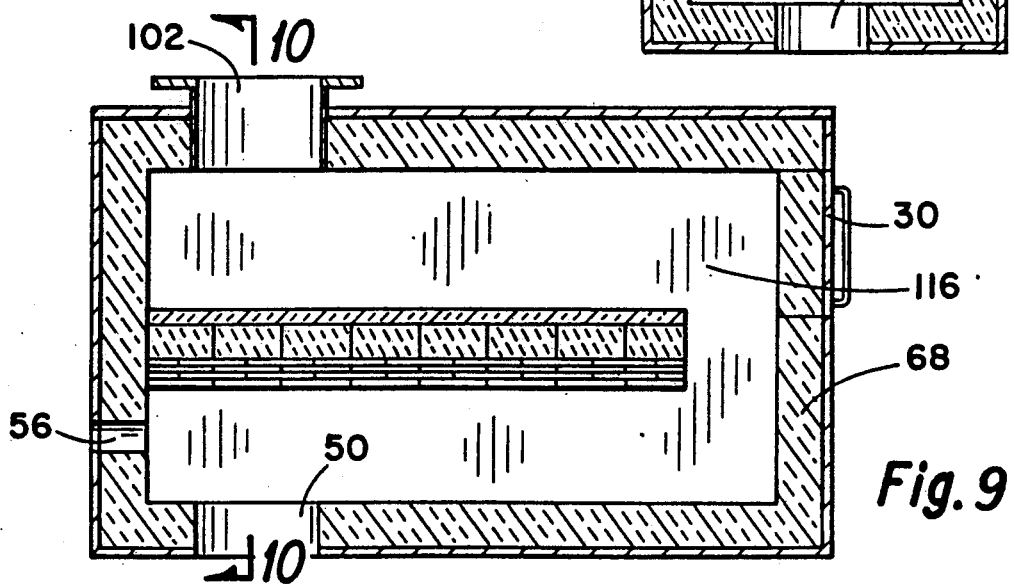
FIG. 9 is a downward sectional view of an alternate embodiment of the secondary incinerator.

FIG. 9 illustrates another variation of the secondary incinerator with a more elongated flow path in the chamber 116.

Figure 10:
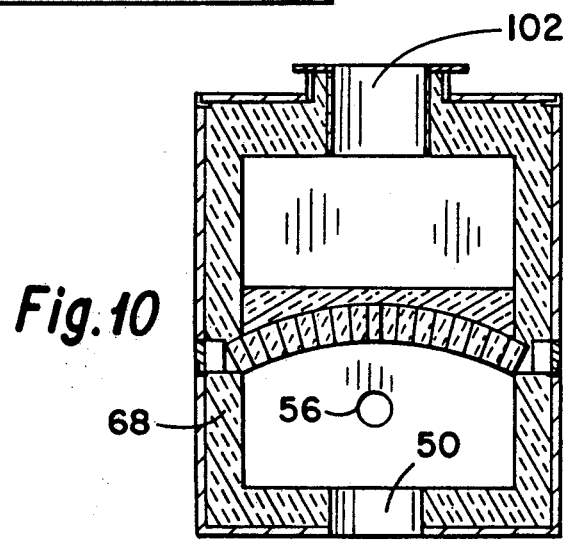
FIG. 10 is a sectional view along line 10-10 in FIG. 9.

FIG. 10 is a section of the embodiment in FIG. 9 along line 10—10 in that figure.

In operation the unit is loaded (usually early in the morning so that the cycle will end before dusk), the door are securely latched, and burn settings are entered into the control panel. As mentioned above, various control settings, and feed back mechanisms are used (all well known in the art). The start button is then pushed which initiates the following sequence:

1. The secondary incinerator burner is ignited and has been preset to burn at about 1800 degrees Fahrenheit.
2. The burndown timer is set for 6-8 hours.
3. The combustion air blower starts supplying air to both primary and secondary chambers.
4. When the secondary incinerator chamber reaches its set point of 1800 degrees Fahrenheit control mechanisms keep the temperature at this point.
5. The primary incinerator burner is ignited and set to burn at 300-400 degrees Fahrenheit. This burner is used for waste ignition only.
6. When the primary incinerator chamber reaches its set point temperature, the primary incinerator burner turns off but the primary incinerator air supply remains on which allows the chamber to gradually increase in temperature to about 1000 to 1400 degrees Fahrenheit.
7. When the secondary incinerator temperature exceeds the set point the combustion air is removed from the primary incinerator and the air control for the secondary incinerator increases to the full maximum position for total combustion air. When the temperature drops to the set points, air flow to primary and secondary incinerators returns to normal.
8. Near the end of the timed burn high air flow is added to the primary incinerator to complete the burn, and to clean the chamber.
9. When the burn timer shuts off, it turns off both the primary and secondary incinerator burners, and starts a cool down timer (usually 4 hours).
10. During the cool down period the air flow is kept on.
11. At the end of the cool down, all power is shut off to the incinerator.

This unit has been used successfully as a medical waste incinerator burning combinations of solids and liquids with metal, fabric, plastic, paper, tissues, biologicals and the like intermixed, and has exhibited complete burns, without slag or residue build up, and without clogging of air supply conduits.

The unit works best as a controlled air incinerator. In the preferred embodiment only enough air is allowed into the primary incinerator chamber to burn approximately 25% of the waste (i.e. sub-stoichiometric amounts of air) and to volatilize the remainder to be burned in the secondary incinerator chamber where additional air is supplied. Any suitable type of fuel may be used, such as propane, natural gas, fuel oil, and the like.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A waste incinerator comprising:
   (a) a primary incinerator with a chamber therein defined by insulated walls having an approximate hourglass shape with a dilated upper portion having a top and a bottom, a dilated lower portion having a roof and a floor, and a constricting portion of said insulated walls forming a division between said upper portion and said lower portion with a central passage therein which communicated between said upper portion and said lower portion; wherein said constriction is further comprised of:
      (i) a top surface forming a downwardly sloping shelf constituting the bottom of said upper portion;
      (ii) a upwardly sloping under surface forming the roof of said lower portion;
   (b) means for feeding waste to be burned into said upper portion of said primary incinerator chamber;
   (c) means for injecting and controlling a flow of fuel and air into said lower portion of said primary incinerator chamber and of igniting said fuel and air so as to burn said waste; wherein said means for injecting air comprises:
      (i) a plurality of generally downwardly directed air conduits in the walls and constricting portion of said lower portion of said primary incineration chamber through which air flow is directed in a generally downward direction toward the floor of said lower portion;
   (d) a secondary incinerator located above said primary incinerator with a secondary incinerator chamber therein and with the upper portion of the primary incinerator chamber connected thereto by a stepped pipe which passes through said top of said upper portion of said primary incineration chamber and thence into said secondary incinerator chamber and through which gases and residue from said burned waste in said primary chamber may rise and flow therethrough into said secondary incineration chamber;
   (e) means for injecting and controlling a flow of fuel and air into said secondary incineration chamber so as to further burn said gases and residue passing through said stepped pipe into said secondary incineration chamber; and
   (f) means for venting the burned contents of said secondary incineration chamber to the exterior.

2. The waste incinerator of claim 1 wherein said flow of fuel and air into said lower portion of said primary incineration chamber has sub-stoichiometric amounts of air.

3. The waste incinerator of claim 1 wherein said flow of fuel and air into said secondary incineration chamber has at least stoichiometric amounts of air.

4. The waste incinerator of claim 1 wherein said chamber in said secondary incinerator contains at least one flow directing baffle therein.

5. The waste incinerator of claim 1 wherein air is injected by means contiguous to said stepped passageway in a direction parallel and co-directional with the flow of said gases from said primary incinerator chamber into said secondary incineration chamber.

6. The incinerator of claim 5 wherein said means to inject said air contiguous to said stepped passageway comprises an air manifold surrounding said passageway, a plurality of upwardly directed air injection nozzles in communication with said manifold, said nozzles oriented substantially upwardly and tangentially to said flow of gases.

7. A waste incinerator comprising:
(a) a primary incinerator with a bifurcated chamber therein, in which said chamber has an upper portion, a lower portion and a constricting portion with a passage therethrough connecting said upper and lower portions;
(b) means for feeding waste to be burned into said upper portion of said primary incinerator;
(c) means for injecting fuel and air into said lower portion of said primary incinerator, and for igniting said mixture to burn said waste; wherein said air injecting means comprises:
(i) a plurality of air conduits generally directed downwardly in the walls of said lower portion of said primary incinerator;
(ii) means for controlling said air flow to give substoichiometric amounts of air;
(d) a secondary incinerator, having a chamber therein, and located upon said primary incinerator, and connected thereto by a stepped pipe which connects said chamber in said primary incinerator to said chamber in said secondary incinerator through which a flow of burn products and gases may pass from said primary incinerator chamber into said secondary incinerator chamber;
(e) at least one flow directing baffle in said chamber of said secondary incinerator;
(f) means for injecting fuel and air, in stoichiometric or greater amounts, into said chamber of said secondary incinerator, and of igniting same; and
(g) means for venting burn products from said secondary incinerator.

8. The waste incinerator of claim 7 wherein air is injected by means contiguous to said stepped passageway in a direction parallel and co-directional with the flow of said gases from said primary incinerator chamber into said secondary incineration chamber.

9. The incinerator of claim 8 wherein said means to inject said air contiguous to said stepped passageway comprises an air manifold surrounding said passageway, plurality of upwardly directed air injection nozzles in communication with said manifold, said nozzles oriented substantially upwardly and tangentially to said flow of gases.

10. A waste incinerator comprising:
(a) a primary incinerator chamber divided into two connected portions: an upper portion and a lower portion, by a constricting division of the walls of said chamber, and in which a central passage therein provides communication between said two portions;
(b) means for introducing waste to be burned into said upper portion of said primary incinerator;
(c) means for injecting fuel into said lower portion of said chamber;
(d) means for injecting air into said lower portion of said chamber to mix with said fuel and of igniting said mixture to provide combustion thereof to burn said waste, said means for injecting air is a plurality of conduits in the walls of said lower portion of said chamber which are directed generally downwardly toward the floor of said lower portion;
(e) means for exhausting burn products from said primary incinerator after burning; and
(f) means for further combusting said exhausted burn products from said primary incinerator.

* * * * *